(12) United States Patent
Gillespie et al.

(10) Patent No.: US 6,863,668 B2
(45) Date of Patent: Mar. 8, 2005

(54) ARTICULATION MECHANISM FOR MEDICAL DEVICES

(75) Inventors: Walter D. Gillespie, San Diego, CA (US); David G. Matsuura, Encinitas, CA (US); Philip J. Simpson, Escondido, CA (US); Gregory M. Smith, Yorba Linda, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 193 days.

(21) Appl. No.: 10/222,446

(22) Filed: Aug. 16, 2002

(65) Prior Publication Data

US 2004/0034343 A1 Feb. 19, 2004

(51) Int. Cl.[7] ............................................... A61B 18/18
(52) U.S. Cl. .............................. 606/7; 606/10; 606/14; 606/19; 604/19; 604/21; 600/101
(58) Field of Search ................................. 606/7, 10–19, 606/41, 46, 78; 607/88, 89, 96, 115; 604/19, 20–22; 600/101, 108

(56) References Cited

U.S. PATENT DOCUMENTS

| | | | |
|---|---|---|---|
| 4,911,148 A | | 3/1990 | Sosnowski et al. |
| 5,381,782 A | | 1/1995 | DeLaRama et al. |
| 5,454,787 A | | 10/1995 | Lundquist |
| 5,469,524 A | * | 11/1995 | Esch et al. .................. 385/118 |
| 5,520,222 A | * | 5/1996 | Chikama .................... 138/118 |
| 5,603,710 A | * | 2/1997 | Easley et al. ................. 606/15 |
| 5,656,011 A | * | 8/1997 | Uihlein et al. .............. 600/146 |
| 5,855,577 A | * | 1/1999 | Murphy-Chutorian et al. . 606/7 |
| 5,972,012 A | | 10/1999 | Ream et al. |
| 5,993,072 A | * | 11/1999 | de Juan et al. ............... 385/78 |
| 6,051,008 A | | 4/2000 | Saadat et al. |
| 6,053,911 A | * | 4/2000 | Ryan et al. .................. 606/33 |
| 6,135,996 A | | 10/2000 | Kolesa et al. |
| 6,258,083 B1 | * | 7/2001 | Daniel et al. ................. 606/15 |
| 6,280,437 B1 | | 8/2001 | Pacala et al. |
| 6,491,626 B1 | * | 12/2002 | Stone et al. ................ 600/141 |
| 6,551,302 B1 | * | 4/2003 | Rosinko et al. ............. 604/505 |
| 6,572,608 B1 | * | 6/2003 | Lee et al. ..................... 606/15 |

FOREIGN PATENT DOCUMENTS

| | | |
|---|---|---|
| DE | 100 34 105 | 4/2002 |
| EP | 0830870 | 3/1998 |
| WO | WO 99/53987 | 10/1999 |
| WO | WO 02/28452 | 4/2002 |

* cited by examiner

Primary Examiner—A. Farah
(74) Attorney, Agent, or Firm—Rajiv Yadav (57) ABSTRACT

An improved articulating device for use with a medical insertion instrument comprising in part a first tube having a plurality of ribs defining a plurality of bending segments, a second tube axially disposed within the first tube, and means for transmitting an axial deflecting pull load. Such device has improved controlled for positioning an end of the device at a selected position within the body. The articulating device has a generally constant moment of inertia and a polar moment of inertia that generally decreases from its proximal to distal end.

13 Claims, 13 Drawing Sheets

ARTICULATION MECHANISM FOR MEDICAL DEVICES

BACKGROUND OF THE INVENTION

1. Field of the Invention

This invention relates generally to the field of articulation devices, and more particularly to the use of articulation devices to treat disorders of the human cardiovascular system.

2. Discussion of the Related Art

Cardiovascular diseases are a leading cause of death in the United States today. To combat this problem, which affects hundreds of thousands of people yearly, doctors and other professionals have developed a variety of procedures and apparatus to fight and treat cardiovascular disease. Percutaneous transluminal coronary angioplasty and atherectomy are two common, minimally invasive procedures used today. In many instances, such relatively non-invasive procedures are considered to be preferable over more invasive procedures. More invasive procedures, such as open-heart surgery, are more traumatic to the patient and require a longer recuperation period.

Another treatment for cardiovascular disease that may be performed in a relatively non-invasive manner is transmyocardial revascularization (TMR). During this procedure, holes are formed in the heart wall to provide alternative blood flow channels for ischemic heart tissue. These holes may be formed by piercing, or alternatively may be cut by a laser. The laser energy may be directed from inside the heart to form a bore through a wall of the heart. Alternatively, a lasing apparatus may be introduced intravenously through a patient's body and into contact with a pre-selected position along the outer wall of the heart.

One approach to laser myocardial revascularization is disclosed in U.S. Pat. Nos. 5,380,316 and 5,389,096, to Aita et al. These references disclose using a deflectable elongated flexible lasing apparatus which is either introduced through a patient's vasculature or alternatively, directly into the patient's chest cavity. However, neither of these references discloses a highly flexible tip that may be controlled with an increased degree of accuracy.

U.S. Pat. No. 4,911,148, to Sosnowski et al. (the "'148 Patent") discloses a deflectable end endoscope with a detachable flexible shaft assembly. The deflectable end segment of the endoscope is equipped with a series of discreet, substantially aligned cutouts. The cutouts are aligned such that they extend along one side of the deflectable end segment of the shaft assembly. While the cutouts provide for increased flexibility of the end segment, the configuration of the invention of the '148 patent does not provide a sufficiently even bend radius. Such bending characteristics are believed to be extremely helpful in properly locating and positioning the apparatus.

The deflectable end segment of the '148 patent may be deflected by pulling on, or otherwise shortening, a control element that is associated with the deflectable end. The imaging fiber associated with the endoscope and the tubing of the deflectable end segment provide sufficient stiffness such that, once the force on the control element is released, they act to straighten the deflected end segment from its deflected configuration. While this mechanism may work with some degree of accuracy, it is desirable to have more control over the end segment when it is straightening. That is, a control element that could function to push, as well as pull, the deflectable end segment is desirable.

The deflectable end segment of the '148 patent is equipped with a plurality of lumens extending through the tubing wall along the length of the deflectable end segment. One drawback associated with such a configuration is that fabrication of plastic elements with holes whose length exceeds more than 10 times their diameter is exceedingly difficult. Typically, the length of a lumen associated with endoscopes such as the endoscope of the '148 patent is roughly 25 to 30 times their diameter. The cost and complications associated with manufacturing such a deflectable end segment are significant, and therefore undesirable.

Clearly, there is a need for a medical articulation device having a controllable, flexible tip that may be easily manufactured, and which may have particular use in connection with performing TMR procedures.

DETAILED DESCRIPTION

An improved articulation device comprising, in part, a first tube having a plurality of ribs which define a plurality of bending segments, a second tube disposed axially within and extending along the length of the first tube having a lengthwise slot, and a push/pull element disposed in the slot and between the first and second tubes for transmitting a deflecting force to the device is disclosed. Such push/pull element may be a wire, thread, rod or any other flexible means.

The device of the present invention is particularly designed for use with a medical insertion device that may be used, for example, inside a patient's vasculature. The design of the device allows it to be selectively moveable into a plurality of predetermined positions within the human body. The user may then maintain the device in a stationary position while a required task is performed. In the preferred embodiment, the articulation device has a generally constant moment of inertia and a polar moment of inertia that generally decreases from its proximal to its distal end. The design of the device enables it to have a generally constant bend radius, with improved control in handling.

This improved articulation device of the present invention is particularly suited for minimally invasive medical procedures, such as TMR. One of ordinary skill in the art would also appreciate that the device may appropriately be used in any area of the art requiring the articulation of a tip around a curve. By way of example, and not of limitation, the present invention may be used as part of a surgical instrument. As part of such an instrument, it may be used to deliver a drug to a selected area of the body, for TMR, i.e. for positioning a laser adjacent an internal organ such as the heart, or for visualization of internal portions of a body.

When used with a medical device such as a catheter or endoscope, the articulation device of the present invention should be securely affixed to the medical device. This securing may be achieved by any means known in the art including, but not limited to, gluing, pressure fitting, welding, clipping and screwing. Alternatively, the articulation device of the present invention may be integrally formed with, or as part of, the medical device. In this way, the user is assured that the articulation device will not become disassociated from the medical device during the procedure.

By way of example, when the articulation device of the present invention is used as part of an endoscope, the device should include a handle, at least one illumination fiber, an imaging fiber, a working channel, and means for controlling all of the same.

Embodiments of the flexible articulation device will now be described in detail, with reference to the drawings, in which like reference numerals designate identical or corresponding elements in each of the several views.

Figure 1A:
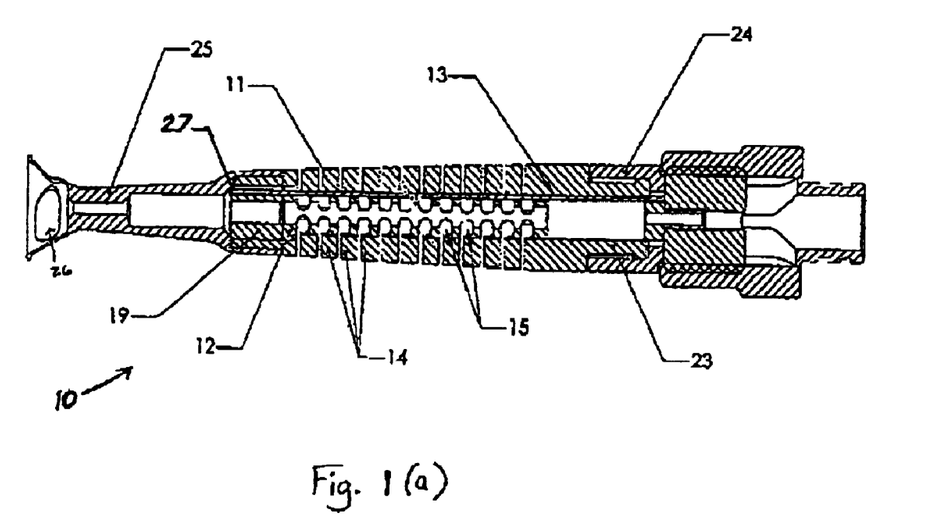
FIG. 1(a) is a perspective view of the articulation device according to one embodiment of the present invention.

FIG. 1(*a*) is a perspective view of the articulation device according to a preferred embodiment of the invention. The articulation device 10 is comprised of first tube 11 having a plurality of ribs 14, a second tube 12 and an articulation push/pull element 13. As shown in FIG. 1(*a*), the circumference of the second tube 12 is varied. Such variation is designed to facilitate manufacture. Additionally, the push/pull element 13 is seen as terminating at 27. However, one skilled in the art would realize that, depending on the degree of angling and control of the device that is required, the push/pull element 13 may extend further along the length of the articulation device 10 or may terminate earlier.

The first tube 11 is a generally elongated structure having a first end 19 that is configured so as to be accurately positioned at a predetermined location and a second end 23 configured to be readily joinable to another medical device. As shown in FIG. 1(*a*), in one embodiment the first end 19 is equipped with a flared nozzle 25 through which a laser, fiber or other device may be positioned at a selected area in the body. The nozzle 25 is also equipped with a plurality of openings 26. The second end 23 is formed with an indented area so that it may securely fit within, and join to, another medical device, generally identified as medical device 24. One skilled in the art will realize that, in alternate embodiments of the invention, the second end 23 may be configured to fit over, slide within or screw into the medical device.

Figure 1B:
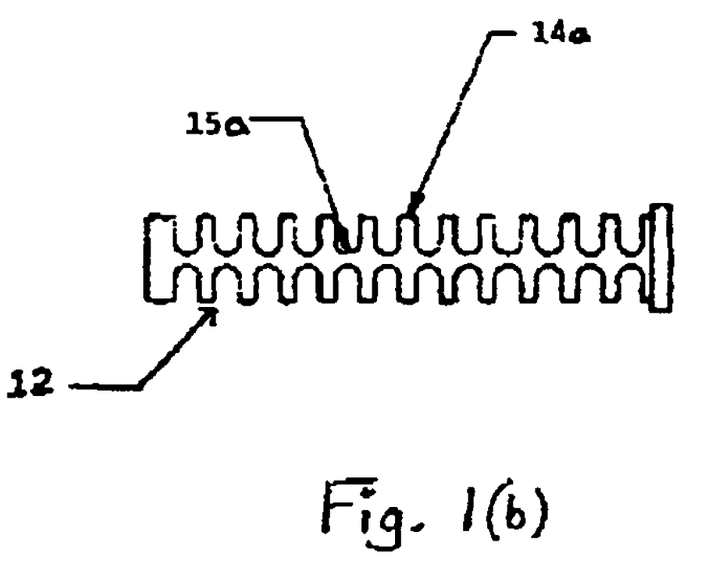
FIG. 1(b) is a perspective view of a portion of the articulation device according to one embodiment of the present invention.

The first tube 11 takes the form of a generally tubular structure having a plurality of generally arcuate ribs 14 extending radially outward along the first tube 11 which define a plurality of bending segments 15. The ribs 14 are located along the length of the first tube 11 to provide for flexibility along the length of the tube. The ribs 14 define a plurality of openings that act as bending segments 15 which may take many different shapes including, but not limited to, semi-circular, triangular, square, rectangular, or oval. As may be seen in FIG. 1(*b*), the second tube 12 also may take the form of a generally tubular structure having a plurality of generally arcuate ribs 14*a* extending radially outward along the second tube 12 which define a plurality of bending segments 15*a*. The ribs 14*a* are located along the length of the second tube 12 to provide for flexibility along the length of the tube. The ribs 14*a* define a plurality of openings that act as bending segments 15*a* which may take many different shapes including, but not limited to semi-circular triangular square, rectangular, or oval.

The ribs 14 are preferably aligned in two rows, one along one side of the articulation device 10, and a second along the generally opposite side of the articulation device 10. Aligning the ribs 14 along opposite sides of the articulation device provides for greater flexibility. However, in other embodiments a configuration in which ribs 14 are present in only one side of tube 11 is within the scope of the invention. The individual ribs 14 may be aligned so that they extend from the articulating device 10 at similar positions along its length. Alternatively, the individual ribs 14 may be aligned so that they alternate, that is, a rib 14 on one side of the articulating device 10 is aligned with the bendable segment 15 between two ribs 14 located towards the other side of the articulating device 10. The articulation device 10 bends generally within the plane as shown in FIG. 1(*a*) and FIG. 1(*b*). This movement causes one set of ribs 14 to become generally closer to one another, and one set of ribs 14 to become generally further spaced apart from one another. The flexibility of the bending segments 15, and thus the articulation device 10, may be varied by changing the dimensions of the ribs 14 and ledges 17 (see FIG. 3), which respond to forces in a manner similar to cantilever beams.

The articulation device 10 may be rotated by the user to view portions of the body that are outside of the bending plane of the present invention. Similar rotation may also be used to steer the articulation device 10. For example, if the user wishes to direct the articulation device 10 towards an area that is located in a direction that is approximately 45° outside of the bending plane, the articulation device 10 may be rotated 45°, and angled, so that any forward motion of the articulation device 10 will move the device towards the selected area. In this manner, the articulation device 10 may be directed as it progresses through the body.

The first tube 11 may be seen as consisting of a continuous multiplicity of short, deflection-limited segments 16 that form a steerable articulation member. In an alternative embodiment of the present invention, these segments 16 may be joined to tube 11 by means known in the art including, but not limited to, gluing, welding, or integral formation.

Figure 2:
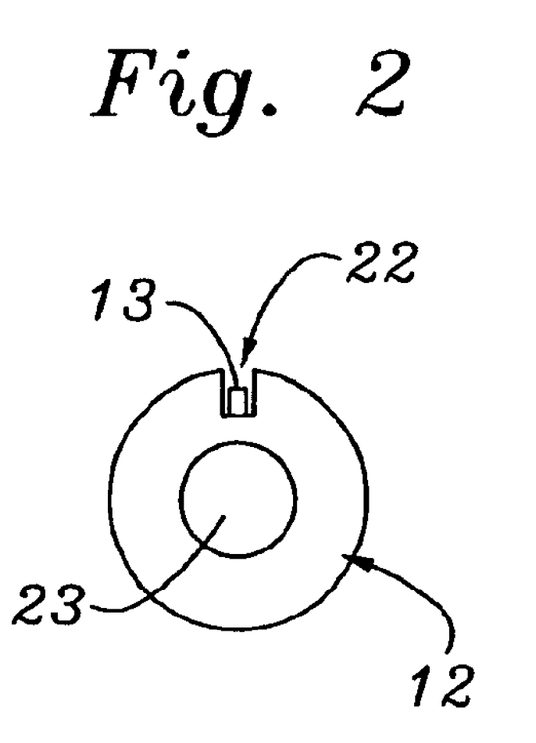
FIG. 2 provides a cross-sectional perspective view of the second tube of one embodiment of the present invention showing how the push/pull element is incorporated into a portion of the articulation device.

FIG. 2 provides a cross-sectional perspective view of the second tube 12 of a preferred embodiment of the present invention showing how the push/pull element 13 is incorporated into the articulation device 10. As may be seen, the second tube 12 defines a slot 22 extending its length. When incorporated into the articulation device, the push/pull element 13 is placed within, and runs along, the slot 22. The presence of the first tube 11 holds the push/pull element 13 in position. FIG. 2 also shows the lumen of the second tube 12, through which fibers, tubes and/or instruments may extend. As one of skill in the art would realize, it is possible to equip the second tube 12 with a plurality of lumen if devices are required to travel separately through the second tube 12. In face, the placement of the push/pull element 13 on the outer portion of the second tube 12 facilitates such plurality of lumens.

As shown in FIG. 2, the second tube has a generally even circumference. However, in an alternate embodiment of the present invention, the second tube 12 may also be equipped with ribs for increased flexibility.

While only one slot 22 and push/pull element 13 is shown in FIG. 2, it should be realized that a plurality of push/pull elements may be utilized in one embodiment of the present invention to provide for greater control of the articulation device 10. These may be incorporated in the present invention through the inclusion of a plurality of slots 22. These slots may be spaced around the periphery of the second tube 12. The push/pull element 13 may be constructed of any suitable material known in the art including, but not limited to, plastic and metal.

Embodiments of the present invention incorporating a slot 22 are typically easier to manufacture than those devices of the prior art that incorporate a lumen for the push/pull element (not shown) which must be formed within and along the length of the articulation device. As noted above, one drawback associated with forming such a lumen is that fabrication of plastic elements with holes whose length exceeds more than 10 times their diameter is exceedingly difficult. The length of a lumen associated with devices such as the present invention may be as long as 30 times their diameter. Clearly, such a design may lead to difficulties in manufacturing. This difficulty is compounded when a plurality of lumens are formed within one structure. In contrast, a slot 22 may be readily incorporated in the second tube 12. This may be done by cutting or otherwise machining the slot 22 from the already-formed second tube 12. Alternatively, the slot may be integrally formed with the second tube 12.

Figure 3:
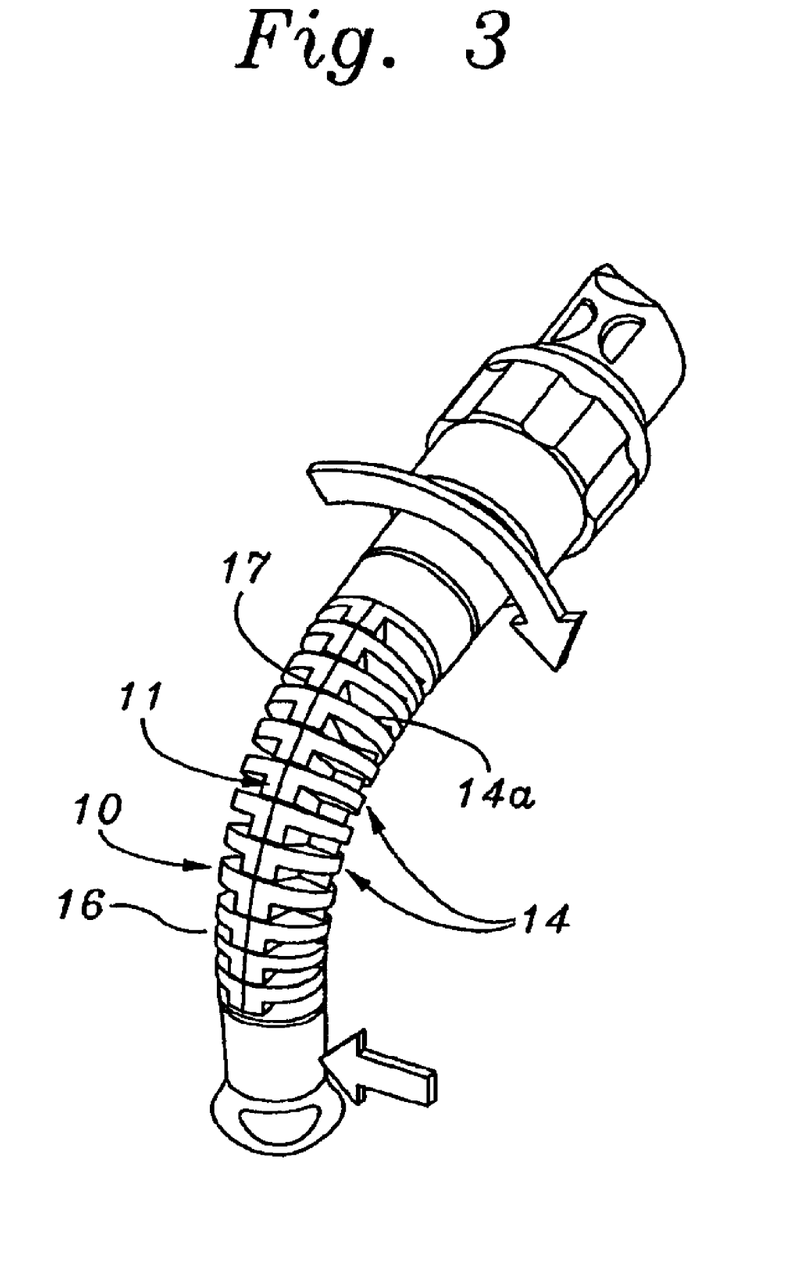
FIG. 3 is a perspective view of the articulation device in a deflected position according to one embodiment of the present invention.

FIG. 3 is a perspective view of an articulation device in a deflected position according to one embodiment of the present invention. In this view, the ribs 14 are to the right and left of the area compressed by the bend. Each rib 14 may be equipped with a generally rectangular ledge 17 extending outward from the rib 14, along the length of the articulating device 10 and located so as to abut an adjacent rib 14. The ledges 17 may be integrally formed with, or attached to, the rib 14 from which they extend. Alternatively, each ledge 17 may be formed with, or attached to, the ribs 14 on either side of the ledge 17. These ledges 17, which may prevent loads imparted on the distal end of the articulation device in the plane of bending from causing over-deflection of the device, are a safety feature of the present invention.

Figure 4A:
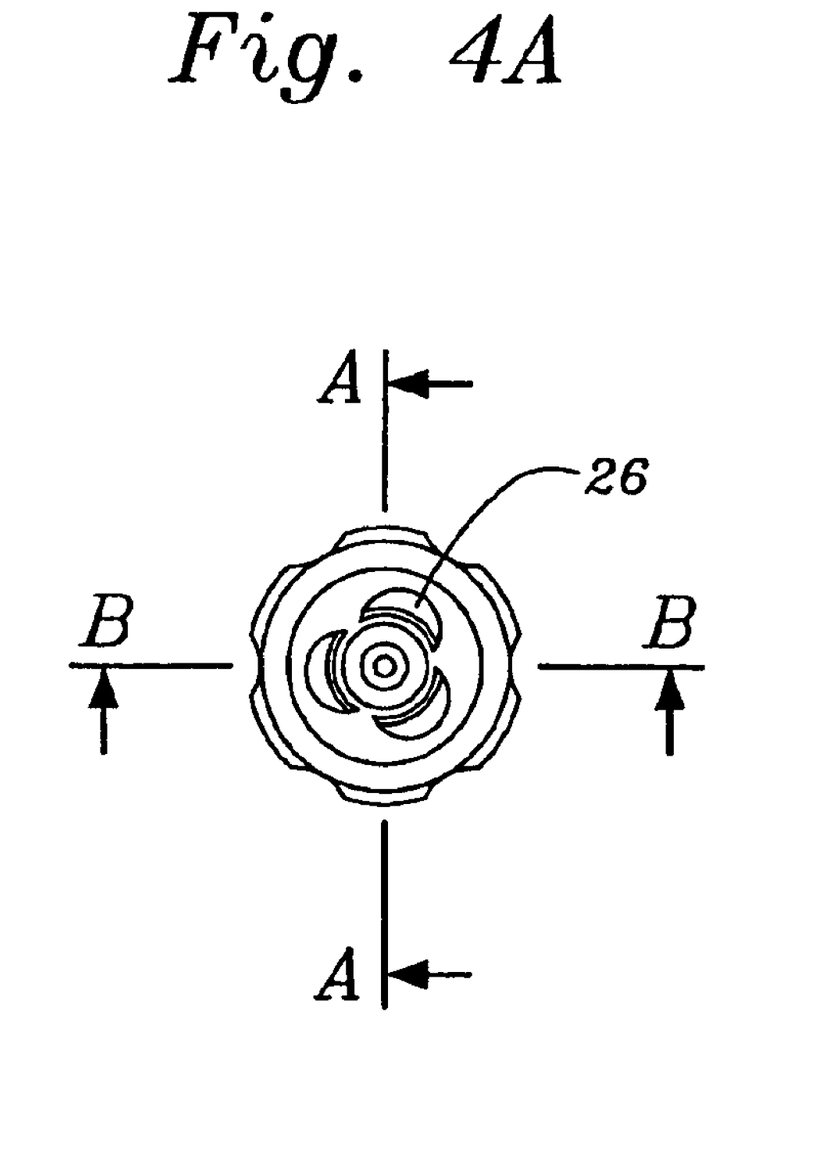
FIG. 4(a) is a perspective view of a cross-section of the articulation device according to one embodiment of the present invention.

FIG. 4(a) is a distal end view of an articulation device 10 according to one embodiment of the present invention. In this depiction, it is possible to see a plurality of crescent-shaped openings 26 on the tip of the articulation device 10.

Figure 4B:
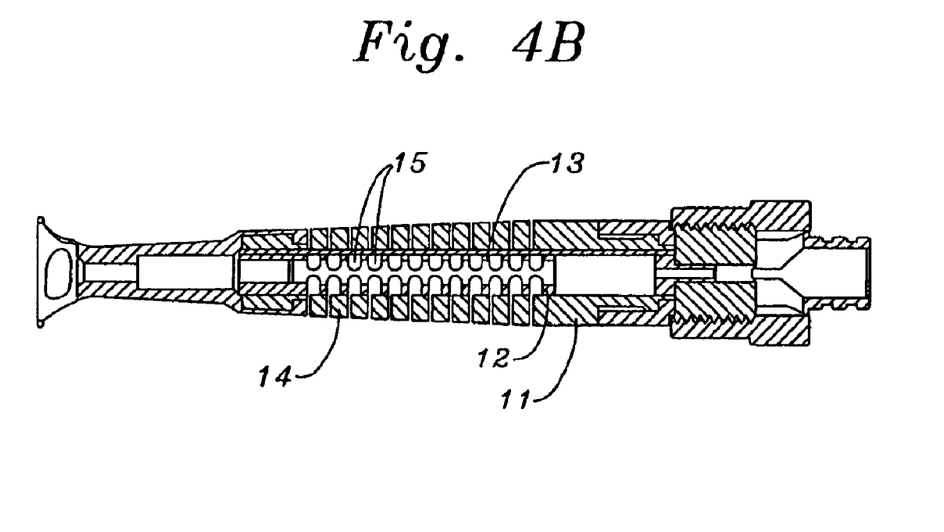
FIG. 4(b) is a perspective view of a liner cross-section of the articulation device according to one embodiment of the present invention.

FIG. 4(b) is a perspective view of a linear cross-section of an articulation device 10 according to one embodiment of the present invention, taken along the B—B line shown in FIG. 4(a). In this view, the ribs 14 may be seen extending along the side of the articulation device 10. The push/pull element 13 and second tube 12 may also be seen.

Figure 4C:
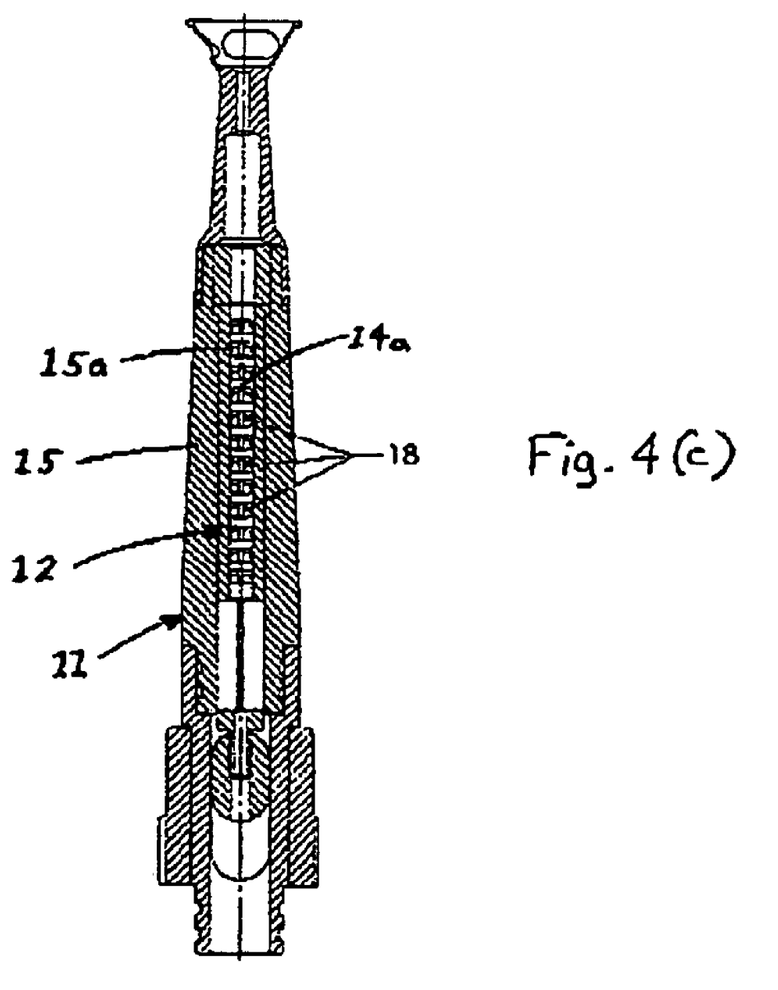
FIG. 4(c) is a perspective view of a second linear cross-section of the articulation device according to one embodiment of the present invention.

FIG. 4(c) is a perspective view of a second linear cross-section of an articulation device 10 according to one embodiment of the present invention, taken along the A—A line shown in FIG. 4(a). This cross-section is taken through the bending segments 15 and 15a in the two tubular structures 11, 12 and since they are circumferentially aligned along generally opposite sides of the articulation device 10 they appear as solid lengths. In this view, the cross-section of openings defined by the bending segments 15 and 15a may be seen as plurality of holes 18.

Figure 5:
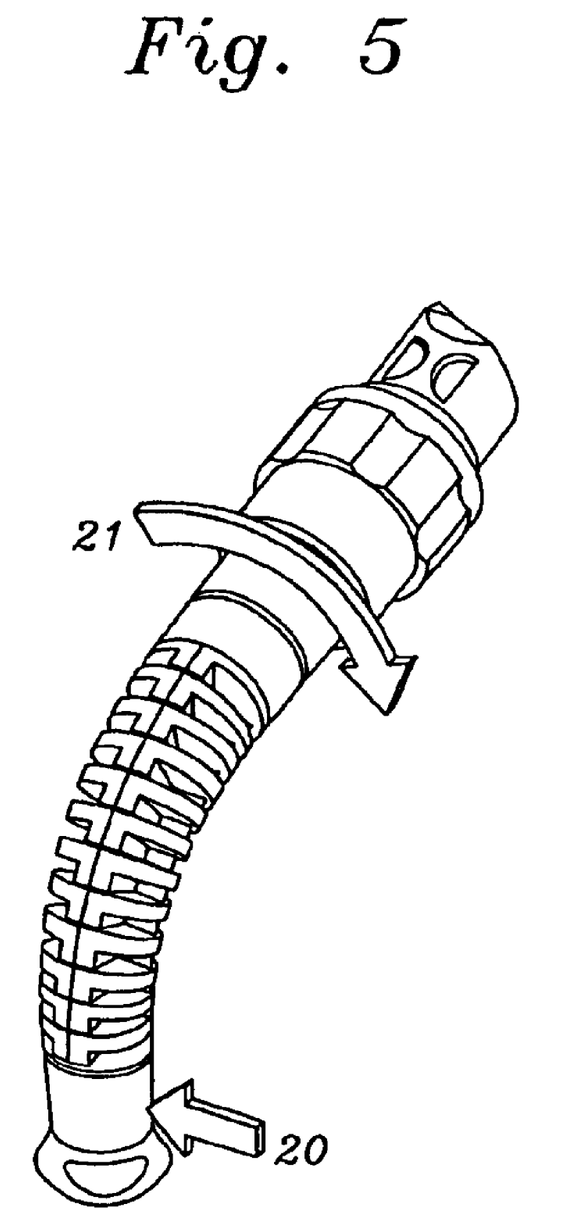
FIG. 5 is a perspective view of the articulation device according to one embodiment of the present invention in which the forces that the articulation device is subject to may be seen.

FIG. 5 is a perspective view of an articulation device according to one embodiment of the present invention in which the forces that the articulation device is subject to may be seen. When the articulation device 10 is bent, it is particularly susceptible to undesired displacement from transverse loads as indicated by arrow 20. Such loads 20 produce a resultant moment 21. The presence of the resultant moment 21 is undesirable, as it provides rotation to the articulation device 10, which impedes the positioning and use of the device.

Figure 6:
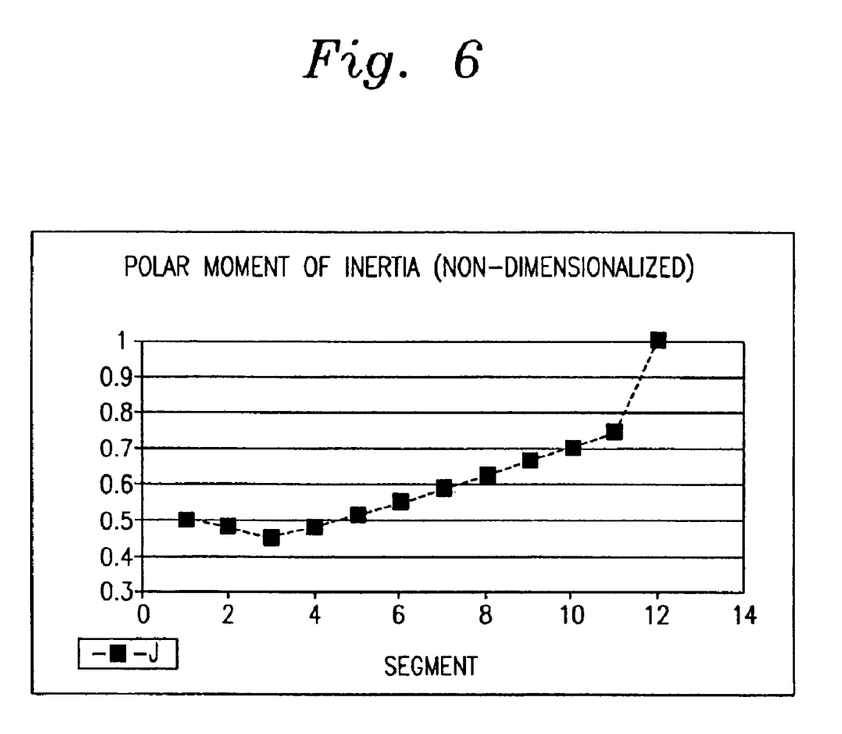
FIG. 6 shows a non-dimensionalized plot of the polar moment of inertia of each segment in the articulation device according to one embodiment of the present invention as compared to the twelfth segment.

It is expected that, during a procedure, the articulation device will frequently be bent at an angle varying from 0° to 90°. During such bending, as noted above, the articulation device is particularly susceptible to undesirable displacement from transverse loads. See FIG. 5. One feature of the present invention that combats such displacement is the selection of the polar moment of inertia of each rib 14. The polar moment of inertia of each bending segment 15 from the distal to the proximal end is generally greater than the one that proceeds it. This may be seen in FIG. 6, which shows a non-dimensionalized plot of the polar moment of inertia of each segment in the articulation mode, as compared to the twelfth segment. This graph shows a general trend of increasing torsional stability from the distal to the proximal end.

Figure 7:
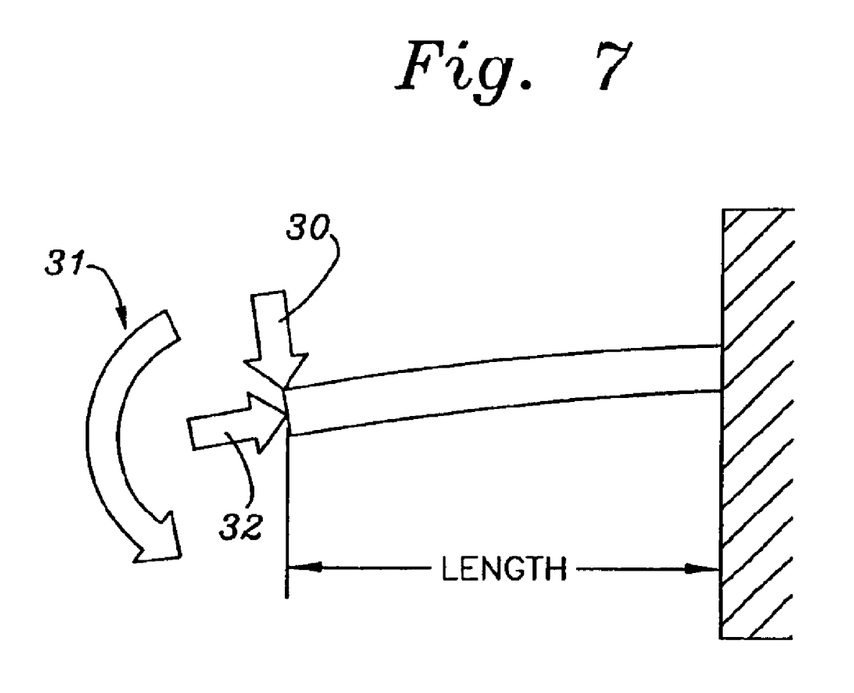
FIG. 7 shows the forces that may be experienced by a rib according to one embodiment of the present invention.

As noted above, the bending segments 15 respond to forces in a manner similar to cantilever beams. FIG. 7 shows the forces which may be experienced by a bending segment 15. The cantilever beam shown in FIG. 7 has a moment 31, a compressive axial load 32 and a downward load 30 applied to its distal end. Knowledge of how these forces affect cantilever beams, and adjusting the dimensions of the ribs 14 to achieve a desired net geometry of the bending segments 15 accordingly, allows for the construction of an articulation device 10 according to one embodiment of the present invention having the desired deflection per segment 16. Selection of the desired deflection per segment 16 allows the articulation device 10 of the present invention to be designed with a constant bend radius.

Since the present invention will frequently be operated while the articulation device is bent, an even bend radius is important. Having an even bend radius helps to ensure that the light fiber does not fail during a procedure. Such a failure could occur, for example, if one or more segments 14 of the articulation device exhibited an extreme deflection.

For purposes of predicting the mechanical behavior of the articulation device, therefore ensuring that the articulation device is designed with an even bend radius, the bending segments 15 have been modeled as a rectangular cantilever beam with a moment, a compressive axial load and a downward load applied to its distal end. FIG. 7 is a free body diagram representing one deflection segment 14 of the articulation device 10. Summing moments about the fixed end of the beam, and integrating twice with respect to the length yields the following deflection equation:

$$Y = (F)\left(\frac{length^3}{4EI}\right) + (M)\left(\frac{length^2}{2EI}\right)$$

Where Y is the downward deflection at the end of the rib 14, F is the load imparted from the internal push/pull element 13, length is the length of the rib 14, E is the elastic modulus of the material said rib 14 would be made of, and I is the section modulus of the rib 14. Angular deflection and maximum stress per segment are determined using this basic equation coupled with the assumption that there will be a constant downward deflection, Y per segment. This approximation allowed for the design of an ideal articulating segment. Such segment provides the desired amount of bend during use.

Figure 8:
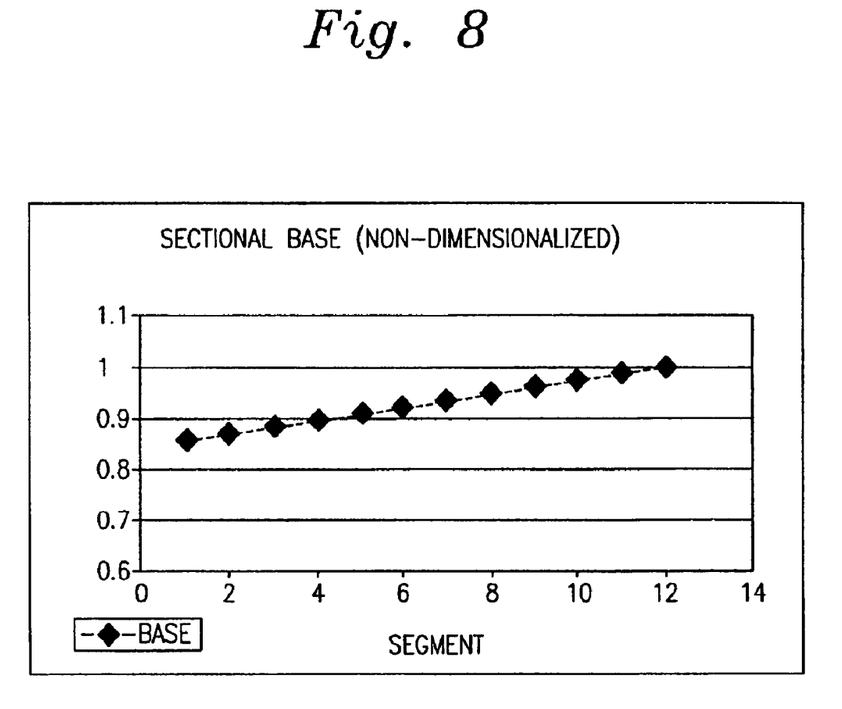
FIG. 8 shows a non-dimensional plot of the base of each bending segment of one embodiment of the present invention as compared to the 12th bending segment.
Figure 9:
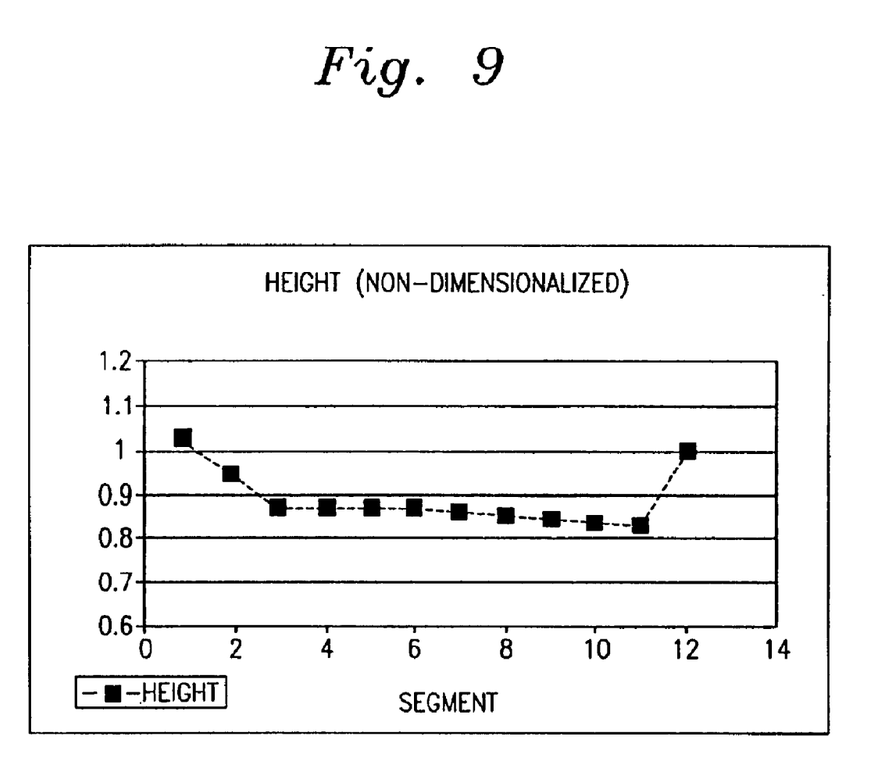
FIG. 9 shows a non-dimensional plot of the height of each rib of one embodiment of the present invention as compared to the 12th bending segment.

In one embodiment of the present invention, the cross-section of the articulation device increases from the distal to the proximal end. In this embodiment, the base width of each cantilever segment also varies from the distal to the proximal end. FIG. 8 shows a non-dimensional plot of the base of each bending segment of this embodiment of the present invention as compared to the 12th bending segment, which is the most proximal bending segment of that embodiment of the present invention. To compensate for the variation in base width, the height of each cantilever segment was selected such that it ensured a desired moment of inertia for each and every segment. FIG. 9 shows a non-dimensional plot of the height of each bending segment of one embodiment of the present invention as compared to the 12th bending segment, which is the most proximal bending segment of that embodiment of the present invention. This figure shows a generally decreasing height from distal to proximal ends.

The moment of inertia of a bending segment 15 is determined by the following equation, where b is the base dimension of the section, h is the height dimension of the section and I is the moment of inertia of the section.

$$I = \frac{1}{12}bh^3$$

If the length of a cantilever beam is held constant, the amount it deflects under identical loading conditions can be altered by changing its cross sectional dimensions. Changing the height of the cross section can have a dramatic effect on its section modulus. When the aforementioned variations in base and height of the device's articulation segments are used to calculate each segment's moment of inertia in the bending plane, one may see a generally constant moment of inertia along the length of the articulation device. Such generally constant moment of inertia may be seen in FIG. 10.

It should be understood by one of ordinary skill in the art that the flexibility of the articulation device 10 may be varied by varying the length of the bending segment 15, the materials from which the articulation device are constructed, and the base dimension, or width, of the bending segment 15.

Figure 10:
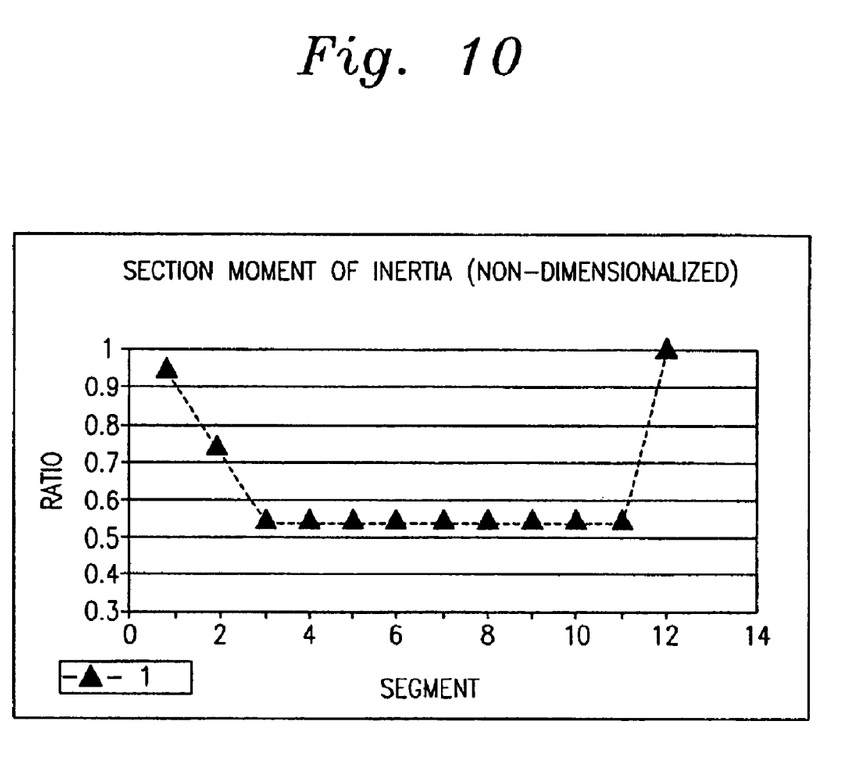
FIG. 10 shows a non-dimensional plot of the moment of inertia of each bending segment of one embodiment of the present invention as compared to the 12th bending segment.

FIG. 10 shows a non-dimensional plot of the moment of inertia of each bending segment 15 of one embodiment of the present invention as compared to the 12th rib, which is the most proximal bending segment 15 of that embodiment of the present invention. As may be seen from the figure, in the embodiment of the present invention from which this data was taken the bending segments 15 have a generally constant section moment of inertia throughout the body of the articulation device 10. However, this section moment of inertia is increased at both ends of the articulation device. In this embodiment of the present invention, segments 1, 2 and 12 have a significantly higher moment of inertia than segments 3 through 11. This increased moment of inertia restricts the magnitude of deflection of that portion of the articulated segment, thus ensuring an even bend radius.

It is desirable to have a gradual transition from the articulating section to the straight sections of the device when the device is articulated. This ensures that the laser fiber will not travel through any extreme curvatures when the device of the present invention is used. Such a gradual transition is achieved by incrementally increasing the section thickness near the proximal and distal ends. This gradual, discrete increase in section thickness reduces the amount each section deflects. A graph showing the section modulus, and hence the ability of the section to bend, of each section relative may be seen at FIG. 10. In this plot, the section modulus of each segment is compared to the section modulus of segment number 12. The incremental decrease in section modulus in segments 1, 2 and 3 indicate each consecutive segment should bend more than the one before it when articulated. The constant section modulus of segment numbers 4 through 11 indicates that these segments should each bend the same amount when articulated. Segment number 12 has a larger section modulus, which indicates that it should bend less than the 7 before it.

While the apparatus described herein is described as particularly useful for the treatment of disorders of the human cardiovascular system, it should be understood by one of ordinary skill in the art that the apparatus may also appropriately be used in any area of the art requiring mechanical fiber optic manipulation.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A flexible articulation device having a generally even bend radius, wherein the device is adapted for attachment to a medical insertion instrument, the device comprising:

a first elongated tubular member having a proximal end and a distal end and a middle portion along its length therebetween, the first elongated tubular member also having, a plurality of ribs extending radially outward therefrom, adjacent ribs defining bending segments therebetween that are not all equal, wherein at least one of the bending segments adjacent the proximal end has a moment of inertia that is greater than the moments of inertia of the bending segments in the middle portion to restrict the magnitude of deflection of the proximal end of the articulation device relative to the middle portion;

a second elongated tubular member axially disposed within the first tubular member and extending along the length thereof; and a flexible push/pull member extending along and joined to the articulation device near the distal end of the first tubular member such that the articulation device is selectively deflectable along the first and second elongated tubular members into a plurality of stationary, predetermined positions within the human body.

2. The flexible articulation device as described in claim 1, wherein the proximal end of the first elongated tubular member includes means for joining the device to the medical insertion instrument.

3. The flexible articulation device as described in claim 1, wherein the distal of the first elongated tubular member includes a flared nozzle configured to form an abutting relationship with a desired internal body member.

4. The flexible articulation device as described in claim 1, wherein the plurality of ribs each include a ledge that abuts an adjacent rib upon deflection of the device and limits the amount of deflection between the adjacent ribs.

5. The flexible articulation device as described in claim 1, wherein the second tubular member has a plurality of ribs extending radially outward therefrom.

6. The flexible articulation device as described in claim 1, wherein the second elongated tubular member further defines a slot extending along an outer surface of the second elongated tubular member within which the flexible push/pull member extends.

7. The flexible articulation device as described in claim 6, wherein the second elongated tubular member further includes a central lumen for passage of medical instruments.

8. The flexible articulation device as described in claim 1, wherein the bending segments in the middle portion have generally constant moments of inertia.

9. The flexible articulation device as described in claim 1, wherein at least one of the bending segments adjacent the distal end has a moment of inertia that is greater than the moments of inertia of the bending segments in the middle portion.

10. The flexible articulation device as described in claim 1, wherein the overall cross-section of the articulation device increases from the distal to the proximal end.

11. A flexible articulation device having a generally even bend radius, wherein the device is adapted for attachment to a medical insertion instrument, the device comprising:

an elongated tubular member defining a first end, a second end, and a plurality of ribs extending radially outward along its length, wherein the ribs define bending segments each having a moment of inertia I, which results in a desired deflection Y according to the following formula:

$$Y=(F)(length^3/4EI)+(M)(length^2/2EI)$$

where Y is the downward deflection at the end of the rib,

F is the load imparted to the bending segment,

M is the moment imparted to the bonding segment, length is the length of the rib, E is the elastic modulus of the material the rib is made of, and I is the section modulus of the bending segment; and a flexible member extending axially disposed within the tubular member and extending along the length thereof, wherein the flexible member is adapted to selectively bend the flexible articulation device into a plurality of predetermined positions.

12. The flexible articulation device as described in claim 11, wherein the first end of the elongated tubular member is adapted for attachment to a medical device.

13. The flexible articulation device as described in claim 11, wherein the second end of the elongated tubular member is joined to a flared nozzle.

* * * * *

UNITED STATES PATENT AND TRADEMARK OFFICE
CERTIFICATE OF CORRECTION

PATENT NO. : 6,863,668 B2  Page 1 of 1
DATED : March 8, 2005
INVENTOR(S) : Gillespie et al.

It is certified that error appears in the above-identified patent and that said Letters Patent is hereby corrected as shown below:

Column 10,
Line 19, after "imparted to the" delete "bonding" and insert -- bending --.

Signed and Sealed this

Fourth Day of April, 2006

JON W. DUDAS
*Director of the United States Patent and Trademark Office*